United States Patent [19]

Kurtz et al.

[11] Patent Number: 4,495,943
[45] Date of Patent: Jan. 29, 1985

[54] ORTHOPEDIC FOOT SPLINT WITH SWIVEL

[75] Inventors: Robert J. Kurtz, New York; Joseph LiCausi, Port Jefferson Station, both of N.Y.

[73] Assignee: Bioresearch, Farmingdale, N.Y.

[21] Appl. No.: 611,713

[22] Filed: May 18, 1984

Related U.S. Application Data

[63] Continuation of Ser. No. 531,583, Sep. 9, 1983, , which is a continuation of Ser. No. 358,531, Mar. 16, 1982, abandoned.

[51] Int. Cl.³ ............................................. A61F 3/00
[52] U.S. Cl. ................................ 128/80 A; 128/87 C
[58] Field of Search ............... 128/80 R, 80 A, 87 R, 128/87 C, 88

[56] References Cited

U.S. PATENT DOCUMENTS

| 2,482,646 | 9/1949 | Brachman et al. | 128/80 A |
| 3,487,829 | 1/1970 | Barnett | 128/80 R |
| 4,249,523 | 2/1981 | Bidwell | 128/80 A |

Primary Examiner—John D. Yasko
Attorney, Agent, or Firm—Larson and Taylor

[57] ABSTRACT

An orthopedic foot splint which is attached to the shoes of a user to correct for a toe-in or toe-out condition is disclosed. The foot splint includes a pair of shoe engaging plates and an elongate connecting mechanism. A swivel is provided between the shoe engaging plate and the end of the connecting mechanism so that the shoe of the user can rotate about a vertical axis. The swivel includes a stop which is adjustable to restrict the movement of the swivel so that the toe or heel of the shoe swivels either towards or away from the connecting mechanism from an initial position where the longitudinal axis of the shoe engaging plate is substantially perpendicular to the longitudinal axis of the connecting mechanism. A mechanism for locking the shoe engaging plate against swiveling movement is also provided. The connecting mechanism can include two bars, a central pivot, a central hinge, and lateral hinges. At least one bar is also laterally extendable according to the needs of the user. In place of a bar, a pair of parellelogram links with a tether can be provided.

11 Claims, 7 Drawing Figures

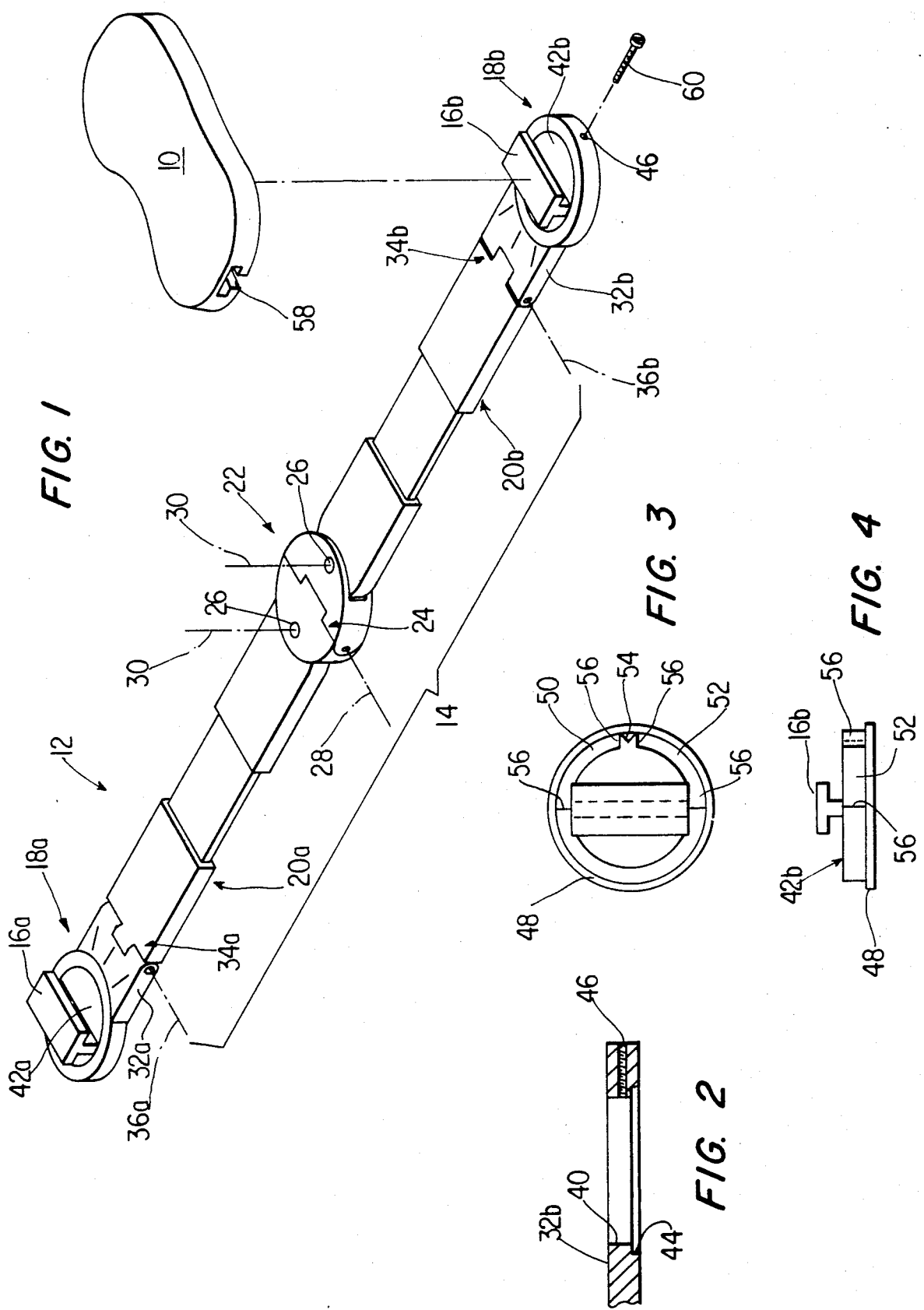

ORTHOPEDIC FOOT SPLINT WITH SWIVEL

This is a continuation of application Ser. No. 531,583 filed Sept. 9, 1983, which is a continuation of Ser. No. 358,531 filed Mar. 16, 1982, now abandoned.

FIELD OF THE INVENTION

This invention relates generally to the field of orthopedic splints which correct for toe-in and toe-out, and more particularly to such a device which corrects one foot or both while allowing some freedom of movement for a normal or abnormal foot.

BACKGROUND OF THE INVENTION

In general, an orthopedic foot splint is useful in correcting bone deformities, particularly in children, by holding the patient's feet at an appropriate corrective angle. Thus, if a patient's feet are abnormally toed-in, it is recommended that the patient wear a splint for a specified period which will hold the feet in a corrective toed-out position. A common type of prior art device, as disclosed in U.S. Pat. Nos. 2,920,620 (Rogers), 4,040,416 (Zentman), and 4,008,129 (DiGiulio), includes a pair of shoes mounted on a flat bar. The shoes in these devices are adjustable on the bar to provide a variety of different toe-in and toe-out angles, but are not otherwise adjustable. Unfortunately, these prior art devices are extremely uncomfortable to the patient as they maintain the feet in almost rigid positions. Even the patent to Zentman which includes a flexible spacer bar to allow a slight amount of verticle movement does little to alleviate this problem. In addition, the patient cannot move except by hopping, which is dangerous and perhaps impossible for young children to perform.

To overcome this almost total lack of mobility and extreme discomfort, prior art devices have been proposed which do allow some movement as well. For instance, in U.S. Pat. Nos. 2,963,020 (Moran) and 4,303,065 (Ericson), a device is disclosed which comprises a separate member attached to each shoe of the patient which members are connected by parallelogram links. These linkages are pivotally attached to each shoe member and this allows movement of the feet both upwards and downwards, and forwards and rearwards. In addition, the length of the linkages is manually adjustable in the former patent. U.S. Pat. No. 3,487,829 (Barnett) also discloses parallelogram links connecting shoe engaging members. In this device, the parallelogram links are attached to the shoe engaging members by ball and socket joints. This device also allows the feet to move forwards and backwards, and upwards and downwards, as well as allowing the ends of the shoes to tilt upwards or downwards somewhat.

In U.S. Pat. No. 4,249,523 (Bidwell), an adjustable orthopedic foot splint to which a pair of shoes is attached is disclosed which maintains a desired angle between the shoes but which otherwise allows virtually full freedom of movement of the shoes.

Disclosed in pending U.S. application entitled "Adjustable Orthopedic Shoe For A Foot Splint", Ser. No. 339,058 filed Jan. 13, 1982, is an orthopedic shoe which is preferably used where the toe of the user is required to be adjusted relative to the heel, and where a foot splint is used to adjust the feet of the user. Disclosed in the pending U.S. application entitled "Orthopedic Foot Splint", Ser. No. 343,555 filed Jan. 28, 1982, is an adjustable orthopedic foot splint which allows virtually full freedom of movement of the feet except for an undesired movement of one foot of the user in front of or too close to the other foot. This is accomplished by using parallelogram links with a tether attached therebetween. Both of these applications are assigned to the assignee of the present application, and are herein incorporated by reference.

SUMMARY OF THE INVENTION

In accordance with the present invention, an orthopedic foot splint is provided for correcting bone deformities by holding the foot to be corrected at a corrective angle. The foot splint of the present invention includes a pair of shoe engaging plates and an elongate connecting means interconnecting the shoe engaging plates. A swivel means is provided between the connecting means and the shoe engaging plates so that the shoe engaging plates can swivel about a vertical axis. A stop means is provided in the swivel means so that the toe or heel of a respective shoe can only swivel either towards or away from the connecting means from an initial position which is substantially perpendicular to the longitudinal axis of the connecting means. With such a device, the shoe engaging plate of the foot requiring correction is restricted from movement in the undesired direction, for example toe-in. However, by use of the selected stop means, the foot to be corrected is allowed a swivel movement to the toe-out position. The other foot, which is frequently without a defect and needs no correction, is also allowed some freedom of movement. Where the foot to be corrected is prevented toeing-in, the normal foot is allowed by the swivel means and stop means to swivel to the toe-in position (although toe-out must be prevented so that toe-in of the other, defective foot, can be prevented).

In the preferred embodiment of the present invention, a lock means is further provided to lock the shoe engaging plate in position and prevent swiveling. The connecting means also includes two bars, having a central pivot, a central hinge, and lateral hinges so that desired movements of the feet are not prevented. Preferably, at least one of the bars also is freely extensible so that the longitudinal length of the connecting means is easily varied according to the needs of the user.

In the other preferred embodiment of the present invention, the connecting means includes at least one pair of parallelogram links. These parallelogram links include a tether attached at an angle to the links so that pivoting in the horizontal plane beyond a predetermined angle can be prevented. A bar and a pair parallelogram links can be provided together with a central hinge and lateral hinges at each end. The parallelogram links can also be provided with a block means to prevent pivoting beyond a predetermined angle on either side of a horizontal line perpendicular to the longitudinal axis of the shoe engaging plate. Two pairs of parallelogram links can also be used.

The swivel means preferably comprises a circular aperture in the shoe engaging plate and a circular disc rotatably mounted in the aperture. By providing two cutouts adjacent one another on the circular disc, a screw mounted to the shoe engaging plate which extends into the cutouts can be used to appropriately limit the rotation of the circular disc to the length of the cutout and the corresponding orientation of the foot of the user.

Other features, objects, and advantages of the present invention are stated in or apparent from the detailed description of the presently preferred embodiments of the invention found hereinbelow.

BRIEF DESCRIPTION OF THE DRAWINGS

FIG. 1 is a perspective view of an orthopedic foot splint according to the present invention.

FIG. 2 is a cross-sectional plan view of the base plate of the swivel depicted in FIG. 1.

FIG. 3 is a top plan view of the circular disc of the swivel depicted in FIG. 1.

FIG. 4 is a front plan view of the circular disc depicted in FIG. 3.

DETAILED DESCRIPTION OF THE PREFERRED EMBODIMENTS

Figure 5:
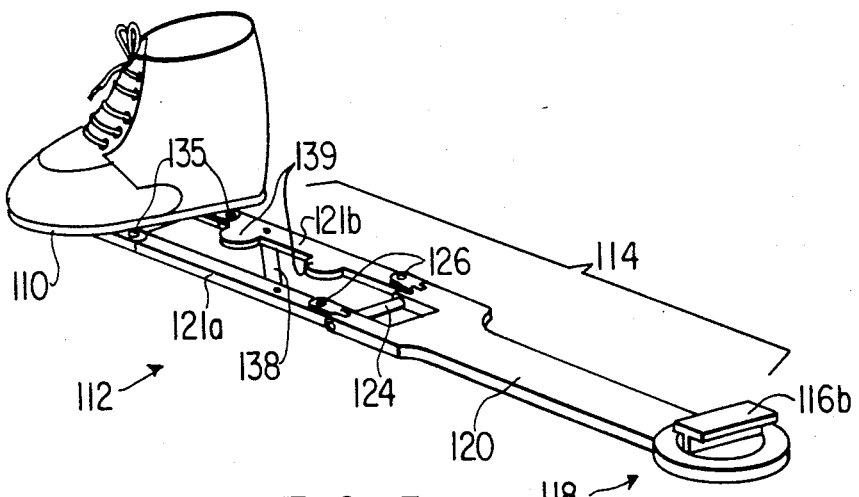
FIG. 5 is a perspective view of an alternative embodiment of an orthopedic foot splint according to the present invention.
Figure 6:
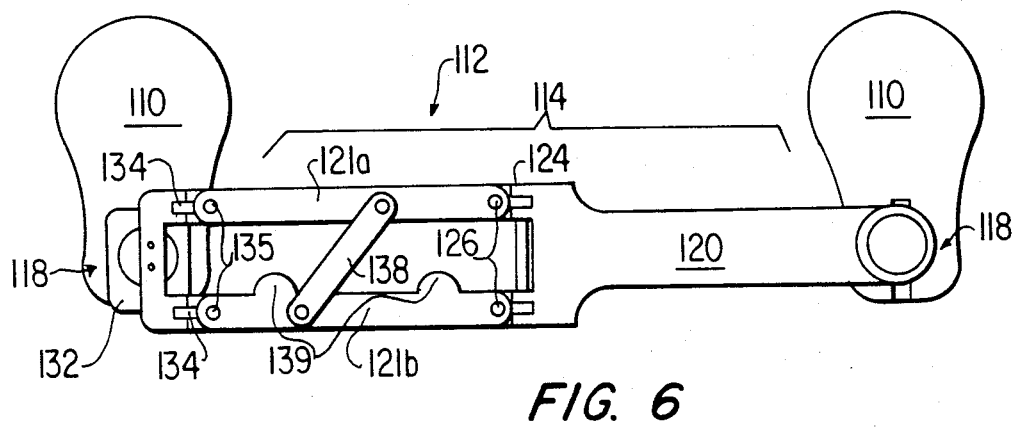
FIG. 6 is a bottom plan view of the orthopedic foot splint depicted in FIG. 5.

With reference now to the drawings in which like numerals represent like elements throughout the several views, a presently preferred embodiment of the present invention is depicted in FIG. 1 along with a shoe plate 10 to which the shoe of the user is attached. A preferred type of shoe is disclosed in the pending U.S. application disclosed above entitled "Adjustable Orthopedic Shoe For A Foot Splint", which is herein incorporated by reference. Orthopedic foot splint 12 includes a connecting means 14, a pair of shoe engaging plates 16a and 16b, and a pair of swivelmeans 18a and 18b.

In the preferred embodiment, connecting means 14 includes two bars 20a and 20b which are interconnected by a joint 22. Preferably, each bar 20a and 20b is freely extensible in the longitudinal direction. This is easily provided by forming bars 20a and 20b from telescoping sections. Conveniently, a stop is also provided to prevent the telescoping sections from being pulled apart. Joint 22 includes a central hinge means 24 as well as a central pivot means 26 so that two planes of motion are possible with bars 20a and 20b. Thus, bars 20a and 20b can pivot relative to one another about axis 28 which is horizontal and substantially perpendicular to the longitudinal axis of connecting means 14. In addition, bars 20a and 20b can pivot in a horizontal plane relative to one another around axes 30 which are vertical. The opposite ends of bars 20a and 20b are connected to a base plate 32a and 32b by lateral hinge means 34a and 34b. In this manner, base plates 32a and 32b can pivot in a vertical plane relative to bars 20a and 20b about axes 36a and 36b, respectively, which are parallel to axis 28.

As shown in greater detail in FIGS. 2, 3, and 4, swivel means 18b includes a circular aperture 40 located in base plate 32b and a circular disc 42 which is received in circular aperture 40. As shown in FIG. 2, circular aperture 40 includes a shoulder recess 44 and a threaded bore 46. As shown in FIGS. 3 and 4, circular disc 42 includes a lower shoulder 48. When circular disc 42 is inserted in circular aperture 40 of base plate 32b, shoulder 48 engages shoulder recess 44. In this manner, circular disc 42 is rotatably mounted in base plate 32b.

Circular disc 42 also includes two cutout portions 50 and 52 which are approximately 90° in length around the circumference of circular disc 42. Located between cutout portions 50 and 52 is a small notch 54. The end faces of cutout portions 50 and 52 form stops 56 whose function will be disclosed subsequently. Mounted to the top of circular disc 42 is shoe engaging plate 16b which has a substantially T-shaped cross section. Referring again to FIG. 1, it can be seen that shoe engaging plate 16b is received in a correspondingly shaped slot 58 in shoe plate 10. A suitable mechanism is then provided to lock shoe plate 10 to shoe engaging plate 16b. Also shown in FIG. 1 is a screw 60 which is received in threaded bore 46 of base plate 32b. By adjusting circular disc 42 appropriately, the end of screw 60 can be located in either of cutout portions 50 and 52 or in notch 54. When the end of screw 60 is located in notch 54, circular disc 42 cannot rotate relative to base plate 32b. However, when the end of screw 60 is located in either of cutout portions 50 and 52, circular disc 42 can rotate approximately 90° relative to base plate 32b until the end of screw 60 contacts stops 56. It should be appreciated that shoe plate 10 extends longitudinally beyond ends of shoe engaging plate 16b so that circular disc 42 is trapped in base plate 32b by shoulder 48 and the bottom of shoe plate 10.

In operation, orthopedic foot splint 12 functions in the following manner. Initially, it must be determined what condition exists in the patient and the appropriate corrective position of the foot which is desired. For example, where the right foot of the patient is toed-in, it is desired to hold the right foot in a substantially parallel or toed-out position. However, where the left foot is normal and requires no corrective action, it is desired to provide as much freedom as possible to the left foot. Therefore, circular disc 42b is initially adjusted so that the end of screw 60 is located in cutout portion 50. Similarly, the end of the screw in swivel means 18a is located in one of the corresponding cutouts in circular disc 42a. In this manner, the right foot is prevented by the movement of circular disc 42b from moving to the toed-in position (i.e., always maintained in the toed-out position), and the right foot is allowed freedom of movement in the toed-out position. Similarly, the other, normal foot is allowed approximately 90° of free movement in either the toed in or toed-out position (preferably, the toed-in position).

By use of orthopedic foot splint 12, an approximately normal walking movement is allowed while the right foot of the user is maintained in the toed-out position. Thus, during walking, as the right foot is brought forward relative to the left foot, the right foot is maintained in the toed-out position be swivel means 18b even though the right foot can be raised or lowered due to lateral hinge means 34a and 34b and central hinge means 24. The bringing forward of the right foot is allowed by the pivoting of bars 20a and 20b relative to one another due to central pivot means 26. The separation of the feet of the user is easily varied due to the telescoping parts of bars 20a and 20b so that pressure on the knee and hip from an improper separation is avoided.

If it is desired to prevent either one of the feet from obtaining a toed-in or a toed-out position, it is also possible to adjust the end of screw 60 so that the end is received in notch 54. In this manner, the respective foot is then maintained between the toed-out and toed-in position. Obviously, both feet could also be maintained in either the toed-in or toed-out position if necessary.

Besides having a toed-in or toed-out condition, it is frequently found that the patient in addition has difficulty with one foot rotating in an inward direction in front of the other foot while walking. While orthopedic foot splint 12 does not correct for this condition, orthopedic foot splint 112 does correct for this condition. Orthopedic foot splint 112 is somewhat similar to the orthopedic foot splint disclosed in the pending U.S. application referred to above entitled "Orthopedic Foot Splint", which application is herein incorporated by reference. In this embodiment, orthopedic foot splint 112 includes a connecting means 114 comprised of a bar 120 and a pair of parallelogram links 121a and 121b. Orthopedic foot splint 112 also includes swivel means 118a and 118b and shoe engaging plates such as 116b. Shoe plates 110 are also shown.

In this embodiment, bar 120 is attached to parallelogram links 121a and 121b by a central hinge means 124. In addition, parallelogram links 121a and 121b are attached to central hinge means 124 by central pivot means 126. A lateral hinge means 134 is also provided to attach parallelogram links 121a and 121b to base plate 132. Attached between links 121a and 121b at an angle thereto is a tether 138. Tether 138 prevents links 121a and 121b from pivoting beyond a predetermined angle. As depicted, tether 138 prevents links 121a and 121b from pivoting forward, but allows pivoting rearward.

In operation, orthopedic foot splint 112 functions in a manner similar to orthopedic foot splint 12. The feet of the user are restrained in a similar manner, and similar freedoms of movement are allowed. However, orthopedic foot splint 112 prevents one foot (the right foot) from moving in front of the other foot. During walking, as the right foot is moved forward, parallelogram links 121a and 121b pivot about central pivot means 126 and a lateral pivot means 135. However, as the right foot is brought laterally adjacent to the left foot, tether 138 prevents parallelogram links 121a and 121b from pivoting in a horizontal plane any further. Therefore, the right foot cannot pivot any further forward as well and is prevented from crossing in front of the left foot. The left foot is then free to move forward in a relatively normal manner. In order to prevent the left foot from moving too far forward, blocks 139 are located on parallelogram link 121a. It should be noted that where orthopedic foot splint 112 is being used to prevent toe-in of the right foot, swivel means 118 of the left foot must be adjusted so that either toe-in (preferably) or no rotating movement is allowed. If swivel means 118 of the left foot is adjusted so that toe-out is provided, this would allow the right foot to cross over towards the left foot during forward movement of the right foot.

Figure 7:
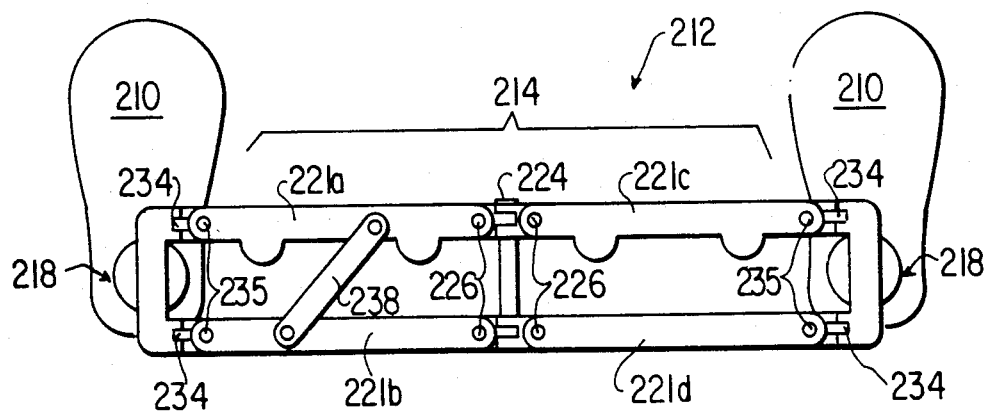
FIG. 7 is a bottom plan view of still another alternative embodiment of an orthopedic foot splint according to the present invention.

Depicted in FIG. 7 is a modified orthopedic foot splint 212 which is similar to orthopedic foot splint 112. In this embodiment, two pairs of parallelogram links 221a, 221b, 221c, and 221d are provided. Connecting the two pairs of parallelogram links are a central hinge means 224, and a central pivot means 226. At the opposite ends of the two pairs of parallelogram links are lateral hinge means 234 and lateral pivot means 235. Orthopedic foot splint 212 is provided with suitable swivel means 218 and shoe plates 210. Connecting one pair of parallelogram links, such as parallelogram links 221a and 221b is a tether 238.

The operation of foot splint 212 is similar to the operation of foot splint 112. However, with foot splint 212, only the swivel means 218 of the foot to be corrected need be adjusted to prevent the undesired positioning of that foot. The other swivel means 218 can be permitted to swivel as desired, for example by removing the screw which limits movement. In this manner, virtually free movement as desired of the normal foot is allowed while the undesired movement of the foot to be corrected is prevented. As with foot splint 112, during walking, the foot to be corrected can only be brought up to a position laterally opposite the normal foot.

Instead of shoe engaging plate 16 as depicted, a number of other shoe engaging plates could be provided. For example, in U.S. Pat. No. 4,249,523 (mentioned above) which patent is hereby incorporated by reference, a shoe engaging plate and an associated plate pivot means could be provided with the present invention to allow rotation of the foot of the user about an axis that is parallel to the longitudinal axis of the connecting means. In addition, the above mentioned patent also discloses a means for exactly positioning the angle of the foot which could be used in conjunction with the swivel means of the present invention.

Thus, while the present invention has been described with respect to exemplary embodiments thereof, it will be understood by those of ordinary skill in the art that variations and modifications can be effected within the scope and spirit of the invention.

We claim:

1. An orthopedic foot splint which is attached to the shoes of a user comprising:
   a pair of shoe engaging plates, each said plate having a longitudinal axis approximately parallel to the longitudinal axis of the shoe which is attachable thereto;
   an elongate connecting means for horizontally interconnecting said pair of shoe engaging plates, said connecting means including
   (a) two elongate sections each of which is pivotally attached at one end to a respective shoe engaging plate, at least one of said two sections being a pair of parallelogram links which are pivotable in a horizontal plane relative to each other and to said shoe engaging plates, and
   (b) a central joint means interconnecting the other end of said sections which allows said sections to pivot in a plane relative to one another;
   a flexible non-extensible tether attached at an angle to said parallelogram links such that said links are prevented from pivoting in the horizontal plane beyond a predetermined angle with respect to the longitudinal axis of the adjacent shoe engaging plate but which can pivot in the opposite direction freely; and
   swivel means provided between said connecting means and at least one of said shoe engaging plates for allowing said shoe engaging plate to swivel about a vertical axis with respect to said connecting means, said swivel means including a stop means for selectively restricting the movement of said swivel means such that the toe or heel of the respective shoe can only swivel toward or away from said connecting means from an initial position where the longitudinal axis of said shoe engaging plate is approximately perpendicular to said longitudinal axis of said connecting means.

2. An orthopedic foot splint as claimed in claim 1 wherein a swivel means is provided between said connecting means and each said shoe engaging plate.

3. An orthopedic foot splint as claimed in claim 1 and further including a lock means which is actuatable for locking said swivel means in a position where the longitudinal axis of said shoe engaging plate is approximately perpendicular to the longitudinal axis of said connecting means so that the swiveling of a respective said shoe engaging plate is prevented.

4. An orthopedic foot splint as claimed in claim 1 wherein at least one of said bars includes an extending means for freely allowing the longitudinal length to vary according to the needs of the user.

5. An orthopedic foot splint as claimed in claim 1 wherein the other of said two sections of said connecting means is a bar; wherein said central joint means includes a central hinge means which connects one end of said bar and said parallelogram links together and which allows said bar and said parallelogram links to pivot about a horizontal axis perpendicular to the longitudinal axis of said connecting means; and further including a lateral hinge means for connecting the other end of said parallelogram links to the respective said swivel means such that said bar and said parallelogram links are allowed to pivot about a horizontal axis perpendicular to the longitudinal axis of said connecting means.

6. An orthopedic foot splint as claimed in claim 5 and further including a block means located between said pair of parallelogram links for preventing said links from pivoting in a horizontal plane beyond a predetermined angle on either side of a horizontal line perpendicular to the longitudinal axis of said shoe engaging plate.

7. An orthopedic foot splint as claimed in claim 1 wherein the other of said two sections of said connecting means is a second pair of parallelogram links; and said central joint includes a central hinge means for interconnecting one end of said pairs of parallelogram links together such that said pairs of parallelogram links are allowed to pivot relative to one another about a horizontal axis perpendicular to the longitudinal axis of said connecting means.

8. An orthopedic foot splint as claimed in claim 3 wherein said swivel means includes a base plate, a circular aperture in said base plate, and a circular disc rotatably mounted in said base plate to which said shoe engaging plate is attached.

9. An orthopedic foot splint as claimed in claim 8 wherein said lock means includes two cutouts adjacent one another in said circular disc, a screw, and a means for mounting said screw to said base plate such that the end of said screw is received in one of said cutouts to limit the rotation of said circular disc to the circumferential length of said cutout.

10. An orthopedic foot splint as claimed in claim 8 and further including a small notch located in said disc between said two cutouts in which the end of said screw can be received to prevent rotation of said circular disc.

11. An orthopedic foot splint as claimed in claim 10 wherein said cutouts extend approximately 90° around the circumference of said circular disc and are located such that the locating of the end of said screw in one said cutout allows the foot of the user to toe-out but not to toe-in while the location of the end of the screw in the other cutout allows the foot of the user to toe-in but not to toe-out.

* * * * *